(12) United States Patent
Hirashima

(10) Patent No.: US 11,642,434 B2
(45) Date of Patent: May 9, 2023

(54) MEDICAL TAPE USING A FILM-FORMING BASE PORTION AND METHOD FOR MANUFACTURING THE SAME

(71) Applicant: YUGENKAISHA CHOURYU, Kosai (JP)

(72) Inventor: Toshifumi Hirashima, Shizuoka (JP)

(*) Notice: Subject to any disclaimer, the term of this patent is extended or adjusted under 35 U.S.C. 154(b) by 0 days.

(21) Appl. No.: 17/594,004

(22) PCT Filed: Aug. 20, 2021

(86) PCT No.: PCT/JP2021/030555
§ 371 (c)(1),
(2) Date: Apr. 24, 2022

(87) PCT Pub. No.: WO2022/137643
PCT Pub. Date: Jun. 30, 2022

(65) Prior Publication Data
US 2022/0241456 A1    Aug. 4, 2022

(30) Foreign Application Priority Data

Dec. 25, 2020   (JP) ................. 2020-216493

(51) Int. Cl.
*A61F 13/00* (2006.01)
*A61L 15/58* (2006.01)
*A61F 13/02* (2006.01)

(52) U.S. Cl.
CPC .......... *A61L 15/58* (2013.01); *A61F 13/0226* (2013.01); *A61F 13/0246* (2013.01);
(Continued)

(58) Field of Classification Search
None
See application file for complete search history.

(56) References Cited

FOREIGN PATENT DOCUMENTS

| CN | 202682175 U | 1/2013 |
|---|---|---|
| JP | 6-13821 U1 | 2/1994 |

(Continued)

OTHER PUBLICATIONS

JP2018075364A Translation (Year: 2018).*
Decision to Grant a Patent; dated Mar. 19, 2021.
ISR: Japanese Patent Office; Sep. 3, 2021.

*Primary Examiner* — Kim M Lewis
(74) *Attorney, Agent, or Firm* — Patshegen IP; Moshe Pinchas

(57) ABSTRACT

A method for manufacturing a medical tape includes: applying a solution polymer serving as an elastic base member portion having an elastic function to an upper layer of a film forming base portion having an inelastic function to form a film of the solution polymer; laminating an adhesion portion having a function to apply and hold the elastic base member portion to a skin on an upper layer of the elastic base member portion, and laminating a release portion having a function to protect the adhesion portion on an upper layer of the adhesion portion; peeling and removing the film forming base portion from the elastic base member portion to obtain the elastic base member portion in a state where a residual shrink force generated by a forming shrinkage of the solution polymer is reduced and to obtain a three-layer structure consisting of the elastic base member portion.

1 Claim, 3 Drawing Sheets

(52) U.S. Cl.
CPC ...... *A61F 13/0253* (2013.01); *A61F 13/0266* (2013.01); *A61F 13/0269* (2013.01)

(56) References Cited

FOREIGN PATENT DOCUMENTS

| JP | H6-13821 U | 2/1994 |
| JP | 11-240830 A | 9/1999 |
| JP | H11-240830 A | 9/1999 |
| JP | 6312915 B1 | 4/2018 |
| JP | 2018075364 A * | 5/2018 |

* cited by examiner

MEDICAL TAPE USING A FILM-FORMING BASE PORTION AND METHOD FOR MANUFACTURING THE SAME

TECHNICAL FIELD

The present invention relates to a method for manufacturing a medical tape that deals with a forming shrinkage.

BACKGROUND ART

Conventionally, for medical industries or the like, a medical tape that uses a film material, such as a polyurethane film, having a function excellent in waterproof performance, moisture permeability, skin followability, and the like has been selected in order to cover and fix a gauze and a pad, fix a surgical tool, such as an indwelling needle or a catheter, cover and protect a wound or a skin, and the like. The indwelling needle is an injection needle used by being inserted into a vein and fixed to a body for blood sampling or drip infusion. The indwelling needle is also used in drip infusion or the like used for about a week.

Since these film materials have a very thin thickness of approximately 10 μm, it cannot independently hold a planar shape and is easily rounded under a natural environment. For this reason, as a support for holding the planar shape, a shape protection cover having stiffness higher than that of an elastic base member of the film material, such as an inelastic plastic film, is laminated with the film material in order to hold the planar shape and prevent formation of wrinkles or the like.

Note that, in its manufacturing process, as means to laminate the support for holding the planar shape and the film material, there has been widely used a method in which, after applying a mixed liquid (a urethane resin liquid and a crosslinking agent liquid) that serves as a raw material of the polyurethane film on an upper layer (one surface) of the inelastic plastic film, the mixed liquid is hardened to form a film, and thus, the polyurethane film is obtained, and simultaneously, the support for holding the planar shape and the film material are laminated.

However, since the above-described method simultaneously performs the film formation of the polyurethane film and the lamination on the support, there is generated a shrink force (an internal stress) remaining due to a forming shrinkage associated with the hardening of the mixed liquid serving as the raw material of the polyurethane film in the polyurethane film. Hereinafter, the "shrink force remaining in the elastic base member during the manufacturing process" will be referred to as a "residual shrink force." Accordingly, in the medical tape that uses the polyurethane film obtained in the above-described method as the elastic base member of the medical tape and the inelastic plastic film as the support of the medical tape, that is, "the medical tape formed by simultaneously performing the film formation of the elastic base member in a film form and the lamination on the inelastic support positioned on an upper layer using the mixed liquid (the urethane resin liquid and the crosslinking agent liquid) serving as the raw material of the polyurethane film, applying an adhesion on a lower layer of the elastic base member, providing an inelastic release sheet on the lowermost layer, and providing an inelastic support for holding the planar shape on an upper layer of the elastic base member" (hereinafter, referred to as a "support-bonded medical tape using inelastic material as the support"), the residual shrink force associated with the forming shrinkage resides in the film material as the elastic base member. That is, when the mixed liquid serving as the raw material of the elastic base member is not attached on the support of the inelastic material, the mixed liquid serving as the raw material of the elastic base member freely shrinks, and thus, the residual shrink force is not generated. Meanwhile, when the mixed liquid serving as the raw material of the elastic base member is well attached on the support of the inelastic material, the mixed liquid serving as the raw material of the elastic base member cannot freely shrink except in a film thickness direction, and thus, the residual shrink force is generated near an attachment interface between the elastic base member and the support of the inelastic material after the film formation.

Note that the support-bonded medical tape using inelastic material as the support is applied in the following sequence: 1) remove the release sheet; 2) apply the tape on a skin; and 3) remove the support. In addition, the residual shrink force of the support-bonded medical tape using inelastic material as the support is not eliminated even by entirely removing the release sheet. After the tape is applied on the skin, the residual shrink force is released by removing the support, and acts as a force to continuously shrink the skin. Since the skin is shrunken, the residual shrink force causes a persistent skin irritation during the application duration.

Here, the residual shrink force existing in the support-bonded medical tape using inelastic material as the support will be described with reference to FIGS. 1 and 2. FIG. 1 is an explanatory diagram illustrating a state in which after a support-bonded medical tape using inelastic material as the support having a bisected support structure is applied on a skin, a support of the thumb side is removed. In order to compare states of the elastic base members underlying the support of the thumb side and the support of the fifth finger side, the support of the thumb side is removed, and the support of the fifth finger side is not removed. While fine wrinkles are observed in the elastic base member of the thumb side from which the support is removed after the tape is applied on the skin, no change is observed in the elastic base member of the fifth finger side from which the support is not removed. FIG. 2 illustrates a state in which the remaining support, that is, the support of the fifth finger side is removed. In FIG. 2, fine wrinkles are also observed in the elastic base member of the fifth finger side. It is conceived that this is because, as the support is removed from the support-bonded medical tape using inelastic material as the support, the elastic base member is released from the support and shrunken so as to exhibit fine wrinkles in the elastic base member, and therefore, a residual shrink force associated with the forming shrinkage exists in the elastic base member. In this manner, in the support-bonded medical tape using inelastic material as the support, the residual shrink force is released by removing the support. Therefore, the residual shrink force associated with the forming shrinkage existing in the support-bonded medical tape using inelastic material as the support can be observed by after applying the medical tape on the skin, removing the support to shrink the elastic base member, thereby causing fine wrinkles to appear in the elastic base member.

Note that, in the medical tape industry, a warning, such as "please apply without pulling (without stretching) because it may cause skin irritation," is called in a handling manual or the like of the product. Therefore, in the medical tape industry, it is inferred that a risk of applying an elastic base member portion of an elastic medical tape on a skin in a "pulled and stretched state" should be sufficiently understood as a common sense of those skilled in the art. Additionally, in the plastic industry, it is conceived to be a common sense of those skilled in the art that applying a solution polymer on an upper layer of an inelastic support (for example, a plastic film) and forming a polyurethane film and laminating it on the support at the same time generates the residual shrink force (the internal stress) associated with the forming shrinkage within the polyurethane film.

On the other hand, in the medical tape industry, it is inferred that there is little recognition (a common sense of those skilled in the art) that the residual shrink force associated with the forming shrinkage exits within the polyurethane film as the elastic base member portion of the support-bonded medical tape using inelastic material as the support. If there is the recognition (the common sense of those skilled in the art) of the existence of the residual shrink force associated with the forming shrinkage in the medical tape industry, and it is understood that the residual shrink force has a harmful effect, there should be a description of warning or the like on the "residual shrink force associated with the forming shrinkage existing in the elastic base member portion" in a handling manual or the like of the product. In a handling manual or the like of a medical tape currently manufactured and sold, there is only a warning that says "if a symptom that seems to be a skin disorder (rash, redness, itching, and the like) appears during use of this product, please stop using and carry out an appropriate treatment," which is a warning that contains a problem of possibly misleading that it is caused by the user's constitutive endogenous cause. Accordingly, there has been a problem that, even though it is a medical tape used by a user with a purpose, the user himself uses the medical tape without recognizing the harmful effect associated with the "residual shrink force associated with the forming shrinkage existing in the elastic base member portion," and moreover, without any preventive measures. Furthermore, a root of this problem is that there is a contradiction that the "residual shrink force associated with the forming shrinkage" is the common sense of those skilled in the art in the plastic industry but it is not the common sense of those skilled in the art in the medical tape industry where products using similar materials are manufactured and sold, and there has been a problem that no countermeasure has been taken for the residual shrink force associated with the forming shrinkage having the harmful effect in the medical tape industry.

In a part, a medical tape (for example, see Patent Document 1) for alleviating a persistent skin irritation during application duration of an elastic base member of an elastic medical tape has been proposed, and the persistent skin irritation during application duration of the support-bonded medical tape using inelastic material as the support caused by the residual shrink force is improved. However, in the medical tape, in the manufacturing process, since it is not possible to simultaneously form the film of the elastic base member portion and laminate it on the stretch prevention portion, and it is essential to laminate the stretch prevention portion in s state where the independently film-formed elastic base member portion is loosened or not extended, problems such as manufacturing equipment and manufacturing cost have emerged in the manufacture of the medical tape, from the viewpoint of efficiency. Accordingly, in the conventional support-bonded medical tape using inelastic material as the support, the production that deals with the residual shrink force associated with the forming shrinkage is not easy, but generates the residual shrink force associated with the forming shrinkage in the elastic base member portion of the medical tape. Thus, it is not easy to alleviate the persistent skin irritation during application duration caused by the residual shrink force associated with the forming shrinkage, and the current situation is that there has been no means that can appropriately solve such a disadvantage.

CITATION LIST

Patent Document

Patent Document 1: Japanese Patent No. 6312915

SUMMARY OF INVENTION

In view of the aforementioned problems, it is therefore an object of the present invention to provide a method for manufacturing a medical tape that has a high effect of alleviating a persistent skin irritation during an application duration caused by a residual shrink force associated with a forming shrinkage of, in particular, a medical tape that has the forming shrinkage by using a solution polymer as a raw material and simultaneously performing a film formation and a lamination in a manufacturing process and aims to be applied on a skin that exhibits an excessive reaction even when a degree of residual shrink force associated with the forming shrinkage as a cause is an insignificant irritation so as to be described as of a level of magnifying lens or microscope, not as of a level of naked eye.

In order to solve the above problems, the present inventor has completed the present invention as a result of repeated diligent studies. That is, a method for manufacturing a medical tape of the present invention comprises: applying a solution polymer serving as an elastic base member portion having an elastic function to an upper layer of a film-forming base portion having an inelastic function to form a film of the solution polymer;

laminating an adhesion portion having a function to apply and hold the elastic base member portion to a skin on an upper layer of the elastic base member portion, and laminating a release portion having a function to protect the adhesion portion on an upper layer of the adhesion portion;

peeling and removing the film-forming base portion from the elastic base member portion to obtain the elastic base member portion in a state where a residual shrink force generated by a forming shrinkage of the solution polymer is reduced and to obtain a three-layer structure consisting of the elastic base member portion, the adhesion portion, and the release portion; and laminating a support portion having a function to hold the elastic base member portion on the elastic base member portion of the three-layer structure.

The medical tape obtained by this manufacturing method includes an elastic base member portion having an elastic function formed of a solution polymer, an adhesion portion having a function to apply and hold the elastic base member portion to the skin, a release portion having a function to protect the adhesion portion and a support portion having a function to hold the elastic base member portion when using the medical tape, in a manufacturing process, wherein it is characterized in that the medical tape is manufactured by peeling and removing a film-forming base portion having an inelastic function enabling the film-formation of the solution polymer from the elastic base member portion and wherein the support portion, the elastic base member portion, the adhesion portion, and the release portion are laminated in this order.

In the method for manufacturing the medical tape of the present invention, steps other than the above steps may be optional and are not particularly limited as long as the effects of the present invention can be obtained.

Advantageous Effects of Invention

According to the method for manufacturing a medical tape of the present invention, the following medical tape, that is, by incorporating a means for reducing the force for continuously shrinking the skin due to the residual shrink force associated with the forming shrinkage of a medical tape that is accompanied by forming shrinkage by simultaneously forming a film and laminating in a manufacturing process using a solution polymer as a raw material as a function, the medical tape, which can reduce the residual shrinkage force associated with the forming shrinkage at the manufacturing stage of the medical tape can be efficiently manufactured. When the medical tape is used, it can be attached to the skin in a state where the residual shrinkage force associated with the forming shrinkage of the medical tape is reduced. Therefore, it is possible to reduce the force for continuously shrinking the skin due to the residual shrinkage force associated with the forming shrinkage of the medical tape, and it is possible to reduce the continuous skin irritation caused by the residual shrinkage force during the application period. This ensures an application on the skin that exhibits an excessive reaction even when a degree of residual shrink force associated with the forming shrinkage as a cause is an insignificant irritation so as to be described as of a level of magnifying lens or microscope, not as of a level of naked eye, thereby ensuring providing a medical tape, an adhesive skin patch, and the like of low irritation. Furthermore, it is possible to prevent inflammation in sebaceous glands or sweat glands, inflammation in the root of hair or its surrounding tissues, a medical instrument pressure-related wound caused by poor blood circulation in skin cells, capillary vessels, or the like due to pressure, and the like.

DESCRIPTION OF EMBODIMENTS

Figure 1:
FIG. 1 is an explanatory diagram illustrating a state in which an inelastic support of a thumb side used for checking the residual shrink force described in paragraph [0007] is removed.
Figure 2:
FIG. 2 is an explanatory diagram illustrating a state in which a support of a fifth finger side as a remaining inelastic support in the explanatory diagram illustrated in FIG. 1 is removed.

In the course of diligent studies, the inventor found that a cause of a residual shrink force in a support-bonded medical tape using inelastic material as the support resided in a forming shrinkage caused by simultaneously performing a film formation and a lamination during manufacturing, and the residual shrink force of the support-bonded medical tape using inelastic material as the support was not eliminated even after a whole release sheet was removed, but after the medical tape was applied on a skin, the residual shrink force was released by removing the inelastic support to become a force that continuously shrinks the skin to shrink the skin, thereby causing a persistent skin irritation during application duration by the support-bonded medical tape using inelastic material as the support. Therefore, the inventor focused on, in the manufacturing process of the medical tape using a solution polymer as a raw material, means that reduces the residual shrink force associated with the forming shrinkage by dealing with the forming shrinkage caused by simultaneously performing the film formation and the lamination from a manufacturing stage.

Here, a skin irritation when the support-bonded medical tape using inelastic material as the support is used for the purpose to, for example, cover and protect wounds or skin will be described. The skin surface has openings of sebaceous glands or sweat glands and also hair. For this reason, the residual shrink force of the support-bonded medical tape using inelastic material as the support continuously deforms the openings of sebaceous glands or sweat glands and occasionally acts as an occluding force so as to generate inflammation (redness, swelling, fever, pain, and dysfunction) in sebaceous glands or sweat glands in some cases. In addition, the continuous skin shrinking force acts as a force to shrink a skin and persistently draw up the hair, so that inflammation occurs in the root of hair or its surrounding tissues in some cases.

Next, a skin irritation when the support-bonded medical tape using inelastic material as the support is used for the purpose to cover and fix a gauze, a pad and the like or fix a surgical tool, such as an indwelling needle or a catheter, will be described. The residual shrink force of the support-bonded medical tape using inelastic material as the support not only acts to fix the indwelling needle, the catheter, or the like but also acts as a force to persistently press a skin at the portion where the indwelling needle, the catheter, or the like is fixed. The residual shrink force is converted into a force of persistently pressing skin cells, capillary vessels, or the like via such surgical tools.

Next, the force of persistently pressing skin cells, capillary vessels, or the like will be described. For example, the blood vessels are stretched all over a human body, and its total extension length is approximately 100,000 km, which reaches around two and a half laps of the earth. In addition, nearly 95% of the blood vessels are capillary vessels. The capillary vessels have a diameter of approximately 7 µm and a wall thickness of 1 µm or smaller, which is significantly thin. For this reason, even for an unaware insignificant pressure, the capillary vessels of skin may be easily deformed or obstructed.

There are approximately five million red corpuscles, used to carry oxygen to cells over the entire body, per a microliter of blood. The red corpuscles are disk-shaped solid materials having recessed centers on both sides with a diameter of approximately 7 to 8 µm and a thickness of approximately 2 µm. The red corpuscles pass through the capillary vessels having a diameter of approximately 7 µm while they are deformed. However, since deformation of the red corpuscles as solid materials is limited, it is difficult to allow the red corpuscles to pass through the capillary vessels even when slight deformation occurs in capillary vessels. In addition, the capillary vessels may be clogged due to occlusion of red corpuscles in some cases. As a result, oxygen deficiency often occurs in cells due to poor blood circulation.

Poor blood circulation caused by pressure may generate a disease in which tissues or cells of skin locally die, such as a decubitus, so called a bedsore. Experimentally, it is said that a decubitus is generated if a persistent pressure is applied to a same part of a body for two hours or longer. For this reason, in order to prevent the decubitus from occurring in the medical industry, it is recommended that a posture be changed at approximately two hour intervals for a bedridden patient who is in a state of lying on a bed or the like, and at approximately thirty minute intervals for a patient who in a state of sitting on a wheelchair or the like. In this manner, the decubitus is generated due to poor blood circulation caused by pressure for several hours.

Furthermore, the recent support-bonded medical tapes using inelastic material as the support have been remarkably improved in skin followability, moisture permeability, waterproof property, skin adherence, and the like, compared with the conventional elastic medical tapes, so that they can be continuously bonded for about a week. For this reason, the support-bonded medical tape using inelastic material as the support are used in many cases to cover and fix a gauze, a pad, and the like, and in particular, fix an indwelling needle for drip infusion or the like for about a week. The force of persistently shrinking skin by covering the surgical tool acts as a force to persistently press a portion of the skin where a medical instrument, such as the indwelling needle or the catheter, is fixed for several days. Therefore, a medical instrument pressure-related wound and the like may occur in the fixed portion. This is inferred to be a period of time far exceeding a limitation of several hours for preventing the decubitus from occurring.

Due to improved qualities of adhesives and elastic base members, a long-time fixation with peel-off durability has been possible, and there has been a product that can be attached for a week or longer. In such a product less likely to be peeled off and excellent for long-time fixation, it is important to inform a warning "when removing the product, please gently remove the product along hair streaks so as not to harm skin" in the handling manual or the like. In order to alleviate skin irritation at the time of removing the product, means that does not forcibly peel the product but leaves it until it peels off is effective. However, use of the means that leaves the product until it peels off naturally increases the application duration, and the persistent skin irritation during the application duration caused by the residual shrink force continuously increases.

Note that, even for insignificant irritation, many patients complain of discomfort and distress. However, if insignificant irritation is persistently applied to the body, "hypaesthesia" which causes dull sensation to a stimulus occurs, so that the number of patients who complain of discomfort or distress is reduced. Although this is generally called "habituation," it does not mean that the stimulus to the body has disappeared, and deformation or occlusion generated in capillary vessels of skin, poor blood circulation, and the like are improved. Even though a degree of the residual shrink force associated with the forming shrinkage described in the paragraphs [0017] to [0023] is an insignificant irritation that may be described as of a level of magnifying lens or microscope, not as of a level of naked eye, it can sufficiently be such a cause.

In this manner, in order to alleviate persistent skin irritation during the application duration, it is important to take the process that leads to the forming shrinkage into consideration and reduce the force of persistently shrinking skin caused by the residual shrink force associated with the forming shrinkage such that the residual shrink force associated with the forming shrinkage is not generated during the film formation in the elastic base member portion of the medical tape.

Therefore, in the present invention, the medical tape is manufactured by using the film-forming base portion. Here, in the manufacturing process of the medical tape using the film-forming base portion, a solution polymer that will later become the elastic base member portion is applied to the upper layer of the film-forming base portion. At this time, the cross-sectional shape of the film-forming base portion and the solution polymer is a rectangle having the same length (see FIG. 3). After that, in the upper layer of the film-forming base portion, forming shrinkage occurs with the curing of the solution polymer, the solution polymer is cured, the forming shrinkage is completed, and the solution polymer is formed into a film and becomes the elastic base member portion. In this process, the upper base portion of the solution polymer that does not come into contact with the film-forming base portion can be freely shrunk with the forming shrinkage. Therefore, at the time when the solution polymer is formed into a film and becomes the elastic base member portion, the residual shrink force associated with the forming shrinkage does not occur and exist in the upper base portion of the elastic base member portion. On the other hand, the lower base portion of the solution polymer in contact with the inelastic film-forming base portion cannot freely shrink except in the film thickness direction due to the forming shrinkage. Therefore, at the time when the solution polymer is formed into the film and becomes the elastic base member portion, the residual shrink force associated with the forming shrinkage is generated and exists in the lower base portion of the elastic base member portion. Therefore, the cross section of the elastic base member portion becomes a trapezoidal shape in which the upper base is shorter than the lower base (see FIG. 4).

Figure 5:
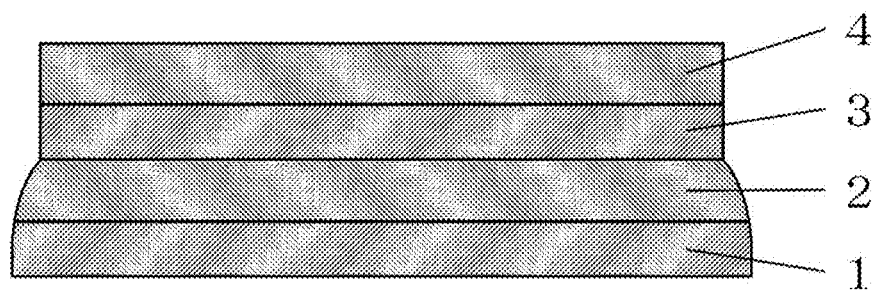
FIG. 5 is a schematic cross-sectional view illustrating a part of the manufacturing process of the medical tape according to the first embodiment of the present invention, and illustrates a state where, after the forming shrinkage of the solution polymer 6 is completed, an adhesive is applied to the upper layer of the elastic base member portion 2 to form the adhesion portion 3 on the two layers composed of the film-forming base portion 1 and the elastic base member portion 2, and the release portion 4 is provided on the upper layer of the adhesion portion 3 to form a four-layer structure.

Next, the adhesion portion and the release portion are laminated on two layers composed of the film-forming base portion and the elastic base member portion (see FIG. 5).

After that, the film-forming base portion is peeled off and removed from the elastic base member portion to form a three-layer structure including the elastic base member portion, the adhesion portion, and the release portion. By removing the film-forming base portion, the residual shrink force associated with the forming shrinkage existing in the lower base portion of the elastic base member portion is released, and it is possible to obtain the elastic base member portion in a state where the residual shrink force generated by the forming shrinkage of the solution polymer is reduced or eliminated. Then, a support portion having a function to hold the elastic base member portion is laminated on the elastic base member portion of the three-layer structure containing the elastic base member portion obtained by the above-mentioned method to form a four-layer structure. Accordingly, a medical tape using a film-forming base portion is completed in a state where the residual shrink force generated by the forming shrinkage of the solution polymer is reduced or eliminated.

The medical tape using the film-forming base portion manufactured as described above is used in the following sequence: 1) remove the release portion; 2) apply the medical tape on the skin by the adhesion portion; and 3) remove the support portion. Thus, by dealing with the forming shrinkage from the manufacturing stage, it is possible to use the medical tape in a state where the residual shrink force generated by the forming shrinkage of the solution polymer is reduced or eliminated. Therefore, in the production of the medical tape using the film-forming base portion, reducing the residual shrink force reduces the force that causes the skin to shrink continuously due to the residual shrink force of the medical tape accompanying the forming shrinkage by using a support-bonded medical tape using inelastic material as the support, particularly by using the solution polymer as a raw material and simultaneously forming the film and laminating it in the manufacturing process, which becomes an effective means to reduce the persistent skin irritation during the application period.

Introducing these effective means to the method for manufacturing a medical tape using a film-forming base portion as a function ensures applying the medical tape on a skin with the residual shrink force of the medical tape being reduced when in use of the medical tape, reducing the force that continuously shrinks the skin due to the residual shrink force of the medical tape, and thus, alleviating the persistent skin irritation during the application duration caused by the residual shrink force, thereby ensuring an application on a skin that exhibits an excessive reaction even with an insignificant irritation. Furthermore, it can be expected that a skin trouble, a medical instrument pressure-related wound, or the like caused by the persistent skin irritation during the application duration is prevented. From this viewpoint, it would be recognized that the conventional support-bonded medical tape using inelastic material as the support, in particular, the medical tape that has the forming shrinkage by using the solution polymer as the raw material and simultaneously performing the film formation and the lamination in the manufacturing process fail to consider the residual shrink force associated with the forming shrinkage.

Therefore, the present inventor selected the material functioning as the elastic base member portion after film formation, from the materials that become cured to form the film after being applied to the upper layer of the film-forming base portion and, as the material of the solution polymer that will later become the elastic base member portion in order to provide a conventional support-bonded medical tape using inelastic material as the support, in particular a medical tape manufactured using a film-forming base portion having a function to reduce the residual shrink force associated with the forming shrinkage of the medical tape with the forming shrinkage by using a solution polymer as a raw material and simultaneously performing a film formation and a lamination in a manufacturing process. Furthermore, selected a material that can be used for medical purposes and has excellent waterproofness, moisture permeability, skin followability, etc. Next, the present inventor selected the material that can be easily removed from the elastic base member portion after the film formation, as the material of the film-forming base portion, from materials that a solution polymer can be applied to the upper layer thereof and a film-like elastic base member portion can be formed into the film and laminated at the same time. In addition, the present inventor selected a medical adhesive material having a function to apply and hold the elastic base member portion to the skin, and having less adhesive residue and keratin damage during peeling, as the material of the adhesion portion, and selected the material of having a function to protect the adhesion portion, as the material of the release portion. Moreover, the present inventor selected the material that can be laminated on the elastic base member portion after removing the film-forming base portion, having a function to hold the elastic base member portion when the medical tape is used, and that can be easily peeled off from the elastic base member portion after being applied to the skin, as the material of the support portion. The inventor came up with an idea of configuring the medical tape using the film-forming base portion using the functions of each material.

By combining these materials, in the manufacturing step of a medical tape using the film-forming base portion, a solution polymer that later turns into an elastic base member portion is applied to an upper layer of the film-forming base portion, and a film formation of the elastic base member portion and a lamination with the film-forming base portion are performed simultaneously. In the upper layer of the film-forming base portion, forming shrinkage occurs with the curing of the solution polymer, the solution polymer is cured, the forming shrinkage is terminated, and the solution polymer is formed into a film and becomes the elastic base member portion. Next, the adhesion portion and the release portion are laminated on two layers composed of the film-forming base portion and the elastic base member portion. After that, the film-forming base portion is removed to form a three-layer structure including the elastic base member portion, the adhesion portion, and the release portion. At this time, by removing the film-forming base portion, the residual shrink force associated with the forming shrinkage existing in the lower base portion of the elastic base member portion is released, and it is possible to obtain the elastic base member portion in a state where the residual shrink force generated by the forming shrinkage of the solution polymer is reduced or eliminated. Then, a support portion having a function to hold the elastic base member portion is laminated on the three-layer structure containing the elastic base member portion obtained by the above-mentioned method, when in use of the medical tape, to form a four-layer structure. Accordingly, it is possible to manufacture a medical tape using a film-forming base portion in a state where the residual shrink force generated by the forming shrinkage of the solution polymer is reduced or eliminated. Accordingly, the present invention has been completed in view of the knowledge that a medical tape can be provided in which: when the medical tape using a film-forming base portion is used, it can be applied to the skin in a state where the residual shrink force is reduced or eliminated; a medical tape using the film-forming base portion can have, as a function, a means to reduce the force that causes the skin to shrink continuously due to the residual shrink force of the support-bonded medical tape using a conventional inelastic material as the support, particularly the medical tape accompanying the forming shrinkage by using the solution polymer as a raw material and simultaneously forming the film and laminating it in the manufacturing process; and the persistent skin irritation during the application duration caused by the residual shrink force is alleviated, thereby ensuring an application on a skin that exhibits an excessive reaction even with an insignificant irritation.

Figure 3:
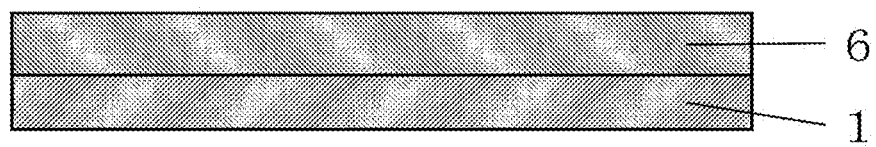
FIG. 3 is a drawing illustrating a part of a manufacturing process of a medical tape according to the first embodiment of the present invention and is a schematic cross-sectional view illustrating a state of a lamination process in which the solution polymer 6 that later turns into the elastic base member portion 2 is applied to the upper layer of the film-forming base portion 1.
Figure 4:
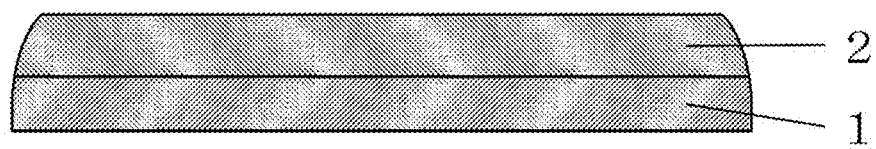
FIG. 4 is a diagram illustrating a part of the manufacturing process of the medical tape according to the first embodiment of the present invention, and it is a schematic cross-sectional view which shows the state where the solution polymer 6 applied to the upper layer of the film-forming base portion 1 is cured and the forming shrinkage is terminated, and the solution polymer 6 was formed into the elastic base member portion 2.
Figure 6:
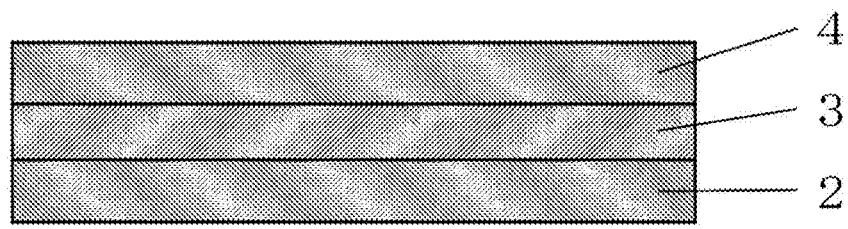
FIG. 6 is a schematic cross-sectional view illustrating a part of the manufacturing process of the medical tape according to the first embodiment of the present invention, and illustrates a state where the film-forming base portion 1 is removed from the state of FIG. 5 and the appearance of a three-layer structure composed of an elastic base member portion 2, an adhesion portion 3, and a release portion 4.
Figure 7:
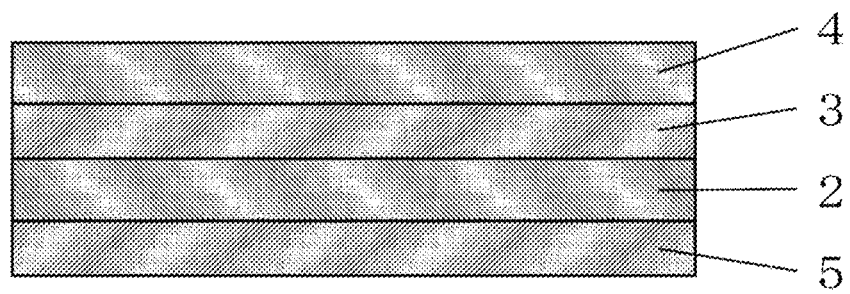
FIG. 7 is a schematic cross-sectional view illustrating a part of the manufacturing process of the medical tape according to the first embodiment of the present invention, and illustrates a state where the support portion 5 is laminated on the three-layer structure including an elastic base member portion 2, an adhesion portion 3, and a release portion 4 to complete the medical tape having a four-layer structure.

A medical tape of the present invention includes, from an upper layer in the following order, the support portion, the elastic base member portion, the adhesion portion, and the release portion. In a manufacturing step, the solution polymer that will later become the elastic base member portion is applied to the upper layer of the film-forming base portion, and a film formation of the elastic base member portion and a lamination with the film-forming base portion are performed simultaneously. At this time, as illustrated in FIG. 3, the cross-sectional shape of the film-forming base portion and the solution polymer is a rectangle having the same length. After that, in the upper layer of the film-forming base portion, forming shrinkage occurs with the curing of the solution polymer, the solution polymer is cured, the forming shrinkage is terminated, and the solution polymer is formed into a film and becomes the elastic base member portion. In this process, the upper base portion of the solution polymer that does not come into contact with the film-forming base portion can be freely shrunk with the forming shrinkage. Therefore, at the time when the solution polymer is formed into a film and becomes the elastic base member portion, the residual shrink force due to the forming shrinkage does not occur and exist in the upper base portion of the elastic base member portion. On the other hand, the lower base portion of the solution polymer that comes into contact with the inelastic film-forming base portion cannot freely shrink except in the film thickness direction due to the forming shrinkage. Therefore, at the time when the solution polymer is formed into the film and becomes the elastic base member portion, the residual shrink force due to the forming shrinkage is generated and exists in the lower base portion of the elastic base member portion. Therefore, as illustrated in FIG. 4, the cross section of the elastic base member portion becomes a trapezoidal shape in which the upper base is shorter than the lower base. Next, after the termination of the forming shrinkage of the elastic base member portion, as illustrated in FIG. 5, an adhesive is applied to the upper layer of the elastic base member portion to form the adhesion portion, and the release portion is provided on the upper layer of the adhesion portion. After that, as illustrated in FIG. 6, the film-forming base portion is removed. By removing the film-forming base portion, the residual shrink force associated with the forming shrinkage existing in the lower base portion of the elastic base member portion is released, and it is possible to obtain the elastic base member portion in a state where the residual shrink force generated by the forming shrinkage of the solution polymer is reduced or eliminated. Then, as illustrated in FIG. 7, a support portion having a function to hold the elastic base member portion is laminated on the three-layer structure containing the elastic base member portion obtained by the above-mentioned method, when in use of the medical tape, to form a four-layer structure. Accordingly, it is possible to complete a medical tape using a film-forming base portion in a state where the residual shrink force generated by the forming shrinkage of the solution polymer is reduced or eliminated, and the medical tape using the film-forming base portion can be used in a state where the residual shrink force associated with the forming shrinkage is reduced or eliminated.

Note that a timing of laminating the adhesion portion and the release portion on the upper layer of the elastic base member portion is preferred to be after the termination of the forming shrinkage (after the termination of the film-forming) when the residual shrink force associated with the forming shrinkage of the elastic base member portion is eliminated. However, it may not always be after the termination of the film-forming in consideration of the selected material of the solution polymer, the manufacturing equipment and manufacturing efficiency, and so on. Even if an inelastic release portion having an adhesion portion is laminated immediately after the solution polymer is applied to the film-forming base portion without waiting for the termination of the film-forming and as a result the residual shrink force associated with the forming shrinkage of the solution polymer remains at an interface portion between the elastic base member portion and the adhesion portion, the residual shrink force associated with the above forming shrinkage is eliminated by removing the release portion when in use, and thus, when in use, the tape can be used in a state where the residual shrink force is reduced or eliminated. Therefore, the timing of laminating the adhesion portion and the release portion may be optional. Note that, in the manufacturing method of the medical tape of the present invention, steps other than the above steps may be optional and are not particularly limited as long as the effects of the present invention can be obtained.

In a medical tape of the present invention, the solution polymer that will later become the elastic base member portion is applied to the upper layer of the film-forming base portion. At this time, the cross-sectional shape of the film-forming base portion and the solution polymer is a rectangle having the same length (FIG. 3). After that, the solution polymer applied to the upper layer of the film-forming base portion is cured and the forming shrinkage is terminated, the solution polymer is formed into a film and becomes the elastic base member portion. The cross section of the elastic base member portion becomes a trapezoidal shape in which the upper base is shorter than the lower base (FIG. 4). Next, the adhesion portion and the release portion are laminated on two layers composed of the film-forming base portion and the elastic base member portion to form a four-layer structure (FIG. 5). After that, the film-forming base portion is removed to form a three-layer structure (FIG. 6). At this time, by removing the film-forming base portion, the residual shrink force associated with the forming shrinkage existing in the lower base portion of the elastic base member portion is released, and it is possible to obtain the elastic base member portion in a state where the residual shrink force generated by the forming shrinkage of the solution polymer is reduced or eliminated. Then, a support portion having a function to hold the elastic base member portion is laminated on the three-layer structure containing the elastic base member portion obtained by the above-mentioned method, when in use of the medical tape, to form a four-layer structure (FIG. 7). Accordingly, it is possible to manufacture a medical tape using the film-forming base portion in a state where the residual shrink force generated by the forming shrinkage of the solution polymer is reduced or eliminated. Note that the degree of the residual shrink force to be reduced is preferred to be eliminated completely. However, since a degree of residual shrink force associated with the forming shrinkage as a cause is insignificant so as to be described as of a level of magnifying lens or microscope, not as of a level of naked eye, the residual shrink force to be reduced may be insignificant, and the effect of the present invention can be sufficiently obtained even if it is insignificant.

Hereafter, although the examples of the present invention will be explained using the drawings, the present invention is not limited thereto. In an appropriate selection/combination of the material constructing the medical tape manufactured using the film-forming base portion, and a manufacturing steps of the present invention, an inelastic plastic film having a function to form a film of the solution polymer is selected as a film-forming base portion, and the solution polymer (a urethane resin liquid and a crosslinking agent liquid) that serves as a raw material of the polyurethane film, which is to be an elastic base member portion later is applied to an upper layer of the film-forming base portion (FIG. 3), after the solution polymer applied to the upper layer of the film-forming base portion is cured and the forming shrinkage is terminated, the solution polymer is formed into a film and becomes the elastic base member portion (FIG. 4), an adhesive is applied as the adhesion portion having a function to apply and hold the elastic base member portion to the skin, and a release portion is provided having a function to protect the adhesion portion, the release portion being formed by coating the peeling agent on the surface of the high-quality paper (FIG. 5), the film-forming base portion is removed (FIG. 6), and accordingly, a medical tape using the film-forming base portion is completed by laminating a support portion having a function to hold the elastic base member portion when in use of the medical tape (FIG. 7). Note that, in the medical tape, the support portion is removed after the tape is applied to the skin by the adhesion portion when in use. In the medical tape using the film-forming base portion, basically, the force that continuously shrinks the skin due to the residual shrink force is reduced, and thus, alleviating the persistent skin irritation during the application duration caused by the residual shrink force. In the present invention, it is essential to reduce the residual shrink force during manufacturing of the medical tape using the film-forming base portion.

A medical tape using the film-forming base portion of a first embodiment of the present invention illustrated in FIG. 3 to FIG. 7 is configured of an elastic base member portion 2, a support portion 5, an adhesion portion 3, and a release portion 4. The elastic base member portion 2 is film-formed by a solution polymer (a urethane resin liquid and a crosslinking agent liquid) 6 as a raw material of the elastic base member portion 2 and has the elastic function. The support portion 5 has the function to hold the elastic base member portion. The adhesion portion 3 has the function to apply and hold the elastic base member portion 2 on a skin. The release portion 4 has the function to protect the adhesion portion 3.

FIG. 3 is a drawing illustrating a part of a manufacturing process of a medical tape using the film-forming base portion according to a first embodiment of the present invention and is a schematic cross-sectional view illustrating a state of a lamination process in which a solution polymer 6 that later turns into an elastic base member portion 2 is applied to an upper layer of a film-forming base portion 1. In the medical tape using the film-forming base portion according to the first embodiment, an inelastic plastic film having a function to form a film of the solution polymer 6 was selected as a film-forming base portion 1, and the solution polymer (a urethane resin liquid and a crosslinking agent liquid) that serves as a raw material of the polyurethane film which later turns into an elastic base member portion 2 was applied to an upper layer of the film-forming base portion 1. At this time, as illustrated in FIG. 3, the cross-sectional shape of the film-forming base portion 1 and the solution polymer 6 is a rectangle having the same length. Note that the reference numeral 1 denotes the film-forming base portion, and the reference numeral 6 denotes the solution polymer.

FIG. 4 is a schematic cross-sectional view illustrating a part of the manufacturing process of the medical tape according to the first embodiment of the present invention, and illustrates the states of the film-forming base portion 1 and the elastic base member portion 2 at the time when, as illustrated in FIG. 3, the solution polymer that later turns into an elastic base member portion 2 in a state of being applied to an upper layer of the film-forming base portion 1 is cured to complete the film-forming, and to terminate the forming shrinkage. At the time illustrated in FIG. 3, the length of the film-forming base portion 1 and the solution polymer 6 was the same. After that, as illustrated in FIG. 4, the length of the upper base of the elastic base member portion 2 (a surface that does not come into contact with the film-forming base portion 1) gradually shortens by the forming shrinkage associated with the curing of the solution polymer 6 to complete the film-forming. At the time when the forming shrinkage terminates, the cross section of the elastic base member portion 2 became a trapezoidal shape in which the upper base (the surface that does not come into contact with the film-forming base portion 1) is shorter than the lower base (the surface that comes into contact with the film-forming base portion 1). This shows that the residual shrink force associated with the forming shrinkage of the solution polymer 6 is generated on the lower base (the surface that comes into contact with the film-forming base portion 1) of the elastic base member portion 2, and that the force exists at the lower base (the surface that comes into contact with the film-forming base portion 1) portion of the elastic base member portion 2. Note that the reference numeral 1 denotes the film-forming base portion, and the reference numeral 2 denotes the elastic base member portion.

FIG. 5 is a schematic cross-sectional view illustrating a part of the manufacturing process of the medical tape according to the first embodiment of the present invention. FIG. 5 illustrates a state where on the upper layer of the elastic base member portion 2 in which the forming shrinkage has been terminated illustrated in FIG. 4, an adhesion is applied as the adhesion portion 3 having the function to apply and hold the elastic base member portion 2 on a skin, and the release portion 4 having the function to protect the adhesion portion 3 is provided on the upper layer of the adhesion portion 3. Note that the reference numeral 1 denotes the film-forming base portion, the reference numeral 2 denotes the forming shrinkage following portion, the reference numeral 3 denotes the adhesion portion, and the reference numeral 4 denotes the release portion.

FIG. 6 is a schematic cross-sectional view illustrating a part of the manufacturing process of the medical tape according to the first embodiment of the present invention, and illustrates the states in which the film-forming base portion 1 is removed, as illustrated in FIG. 5, after an adhesive is applied to the upper layer of the elastic base member portion 2 to form the adhesion portion 3, and the release portion 4 is provided on the upper layer of the adhesion portion 3. By removing the film-forming base portion 1, the residual shrink force of the elastic base member portion 2 associated with the forming shrinkage existing in the lower base (the surface that comes into contact with the film-forming base portion 1) portion of the elastic base member portion 2 was released, and the length of the upper base portion and the lower base portion of the elastic base member portion 2 became the same. This shows that, in a prior art, a generation of the residual shrink force associated with the forming shrinkage, which has been hardly prevented, was successfully reduced in a manufacturing process of the medical tape using the film-forming base portion of the present invention. Note that the reference numeral 2 denotes the elastic base member portion, the reference numeral 3 denotes the adhesion portion, and the reference numeral 4 denotes the release portion. FIG. 7 is a schematic cross-sectional view illustrating a part of the manufacturing process of the medical tape according to the first embodiment of the present invention, in which the medical tape using the film-forming base portion is completed, as illustrated in FIG. 6, by laminating the support portion 5 on the surface on an opposite side facing the surface that comes into contact with the adhesion portion 3 of the elastic base member portion 2 using an adhesive after the film-forming base portion 1 is removed and the length of the upper base portion and the lower base portion of the elastic base member portion 2 becomes the same. Note that the reference numeral 2 denotes the elastic base member portion, the reference numeral 3 denotes the adhesion portion, the reference numeral 4 denotes the release portion, and the reference numeral 5 denotes the support portion.

The medical tape using the film-forming base portion is used in the following sequence: 1) remove the release portion; 2) attach to the skin by the adhesion portion; and 3) remove the support portion, which is the same procedure of using "support-bonded medical tape using inelastic material as the support" manufactured by the prior art, and thus confusion when in use can be prevented. Also, in a medical tape using the film-forming base portion, a generation of the residual shrink force associated with the forming shrinkage of the elastic base member portion, which has been hardly prevented in the prior art, is suppressed in a manufacturing process, and it is possible to obtain an elastic base member portion in which the residual shrink force associated with the forming shrinkage was reduced or eliminated, compared to the prior art. Therefore, even when the support portion is removed after being applied to the skin, no clear change occurs in which the elastic base member portion shrinks, unlike a support-bonded medical tape using an inelastic material as the support of the prior art.

The medical tape using the film-forming base portion is completed by laminating a support portion having a function to hold the elastic base member portion after removing the film-forming base portion and reducing or eliminating the residual shrink force associated with the forming shrinkage that exists in the elastic base member portion in a manufacturing process, such that the elastic base member portion in a state where the residual shrink force associated with the forming shrinkage is reduced or eliminated compared to the prior art is obtained. Therefore, the medical tape using the film-forming base portion can be applied to the skin in a state where the residual shrink force is reduced. Accordingly, the force that continuously shrinks the skin due to the residual shrink force of a support-bonded medical tape using an inelastic material as the support is reduced, and thus, alleviating the persistent skin irritation during the application duration. Therefore, in a manufacturing method of the medical tape using the film-forming base portion of the present invention, it is possible to introduce, as a function, a means for reducing the force that continuously shrinks the skin due to the residual shrink force associated with the forming shrinkage of the support-bonded medical tape using an inelastic material as the support of the prior art, and the medical tape is applied on a skin with the residual shrink force of the medical tape being reduced when in use of the medical tape using the film-forming base portion, reducing the force that continuously shrinks the skin due to the residual shrink force of the medical tape, and thus, alleviating the persistent skin irritation during the application duration caused by the residual shrink force. This ensures an application on the skin that exhibits an excessive reaction even when a degree of residual shrink force associated with the forming shrinkage as a cause is an insignificant irritation so as to be described as of a level of magnifying lens or microscope, not as of a level of naked eye, thereby ensuring providing a medical tape, an adhesive skin patch, and the like of low irritation.

Specifically, in the first embodiment of the present invention, an urethane resin liquid and a crosslinking agent liquid are used as a solution polymer 6, a polyurethane film formed of the solution polymer 6 and having the elastic function is used as the elastic base member portion 2, an inelastic plastic film having a function to form a film of the solution polymer is used as the film-forming base portion 1, an acrylic adhesive having a function to apply and hold the elastic base member portion 2 to a skin is used as the adhesion portion 3, a peeling sheet formed by coating the peeling agent on the surface of the high-quality paper is used as the release portion 4, the inelastic plastic film used as the film-forming base portion 1 is reused after being removed from the elastic base member portion 2 as the support portion 5. In a manufacturing step, an urethane resin liquid and a crosslinking agent liquid which are a solution polymer 6 is applied to an upper layer of the inelastic plastic film which is the film-forming base portion 1, and a film formation of the polyurethane film which is an elastic base member portion 2 and a lamination with the film-forming base portion 1 are performed simultaneously. The solution polymer 6 applied in the upper layer of the film-forming base portion 1 is cured, the forming shrinkage is terminated, and the solution polymer 6 is formed into a film and becomes the elastic base member portion 2. After the upper base portion of the elastic base member portion 2 is shortened than the lower base portion by the forming shrinkage of the solution polymer 6, an acrylic adhesive is applied as an adhesion portion 3 having a function to apply and hold the elastic base member portion 2 to the skin. A release portion formed by coating the peeling agent on the surface of the high-quality paper is provided as a release portion 4 having a function to protect the adhesion portion 3, and the film-forming base portion 1 is removed from the elastic base member portion 2. After that, the inelastic plastic film that has been used as a film-forming base portion 1 and removed in a manufacturing process is reused and laminated as a support portion 5. Note that, although not illustrated, as a means for laminating the film-forming base portion 1 that has been removed in the manufacturing process on the elastic base member portion 2 as a support portion 5, the solution polymer 6 that serves as a raw material of the polyurethane film that later turns into an elastic base member portion 2 is extremely thinly applied on one side of the support portion 5 so as to exhibit a role as an adhesive. In this manner, in the present invention, the support portion may be used as a film-forming base portion.

Also, in the first embodiment, while an urethane resin liquid and a crosslinking agent liquid are used for the material of the solution polymer, the material of the medical solution polymer may be any material that is applied to the upper layer of the film-forming base portion, that has the elastic function after the film-forming, and that can have an adhesion portion on the upper layer. Further, the material may be any solution polymer material which can provide the appropriate function to correspond to the usage such as to cover and fix a gauze, a pad and the like, fix a surgical tool such as an indwelling needle or a catheter, cover and protect a wound or a skin, and the like, or may use other new material and the like. Further, while the inelastic plastic film is used for the material of the film-forming base portion, the material may be any material that has the upper layer to which the solution polymer is applied, and that has the function to form a film of the solution polymer. Still further, in consideration of manufacturing equipment and manufacturing efficiency and so on, a work table and so on may be used in place of the film-forming base portion in some cases. While the acrylic adhesive is used for the material of the adhesion portion, the material of the adhesion portion may be any adhesion that has the function to apply and hold the elastic base member portion on a skin and is usable for medical treatment, and the adhesion may be applied partly or entirely to correspond to the usage. While the release sheet formed by coating the release agent on the surface of the high-quality paper is used for the material of the release portion, any material may be used as long as it has the function to protect the adhesion portion.

Still further, while the inelastic plastic film that has been used as the film-forming base portion 1 and removed in the manufacturing process was reused for the material of the support portion, the material may be any material that has a function to hold the elastic base member portion when in use of the medical tape. Still further, each portion of the medical tape using the film-forming base portion may be provided with other function to correspond to the usage, design, convenience, and the like, and is not particularly limited as long as the effects of the present invention can be obtained.

The medical tape obtained by the method of production of the present invention illustrated in FIG. 3 to FIG. 7 all ensures manufacturing the medical tape from which the residual shrink force associated with the forming shrinkage of the solution polymer is reduced in the manufacturing process by introducing the means for reducing the force to continuously shrink a skin caused by the residual shrink force associated with the forming shrinkage of the support-bonded medical tape using inelastic material as the support in the prior art to the medical tape as a function. Therefore, the medical tape manufactured using the film-forming base portion can alleviate the persistent skin irritation during the application duration caused by the residual shrink force by applying the medical tape on a skin in the state where the residual shrink force associated with the forming shrinkage is reduced and reducing the force to continuously shrink a skin caused by the residual shrink force associated with the forming shrinkage of the medical tape. This ensures an application on the skin that exhibits an excessive reaction even when a degree of residual shrink force associated with the forming shrinkage as a cause is an insignificant irritation so as to be described as of a level of magnifying lens or microscope, not as of a level of naked eye, thereby ensuring providing a medical tape, an adhesive skin patch, and the like of low irritation. Preventions of inflammation in sebaceous glands or sweat glands, inflammation in hair roots and surrounding tissues, medical instrument pressure-related wounds caused by poor blood circulation of cells of skin, capillary blood vessels, and the like caused by pressure, and the like can be expected.

While the example where the medical tape has a shape of rectangular has been described in the first embodiment above, any shape can be selected for the shape of the medical tape to correspond to the usage. For example, a rolled shape and a sheet shape are possible, and a shape that fits each part of body is also possible. While the medical tape is basically configured of the support portion, the elastic base member portion, the adhesion portion, and the release portion in this order, a gauze, a pad, and the like may be provided on the lower layer of the adhesion portion to correspond to the usage, design, convenience, and the like. Note that while the present invention is based on the application on a skin in a closely contacted manner, the medical tape may be applied via a protecting material and the like for protecting the skin from the medical adhesive and the like in some cases.

While all the residual shrink force associated with the forming shrinkage is preferred to be eliminated, a state where it is slightly reduced is also possible. This is because, as described in the paragraphs [0017] to [0024], the degree of residual shrink force associated with the forming shrinkage that this patent is solving is not of a level of naked eye, but is of a level of magnifying lens or microscope. In this description, the process from the manufacturing of the medical tape to the application is described, and "when in use" and "during application duration" are defined as follows. "When in use" represents the duration from removing the release portion, applying on a skin, until removing the support portion following the procedure of using the medical tape. "During application duration" represents the duration where the medical tape using the film-forming base portion is continuously applied.

Note that the function of the medical tape according to the present invention is effectively applied to a medical tape aiming to be applied to a human body. For example, since a skin irritation hypersensitivity patient severely reacts to even an insignificant skin irritation, the use of medical tapes containing percutaneously absorbable drugs is postponed in some cases. However, since it is possible to alleviate the insignificant skin irritation by using the medical tape manufactured using the film-forming base portion, obtained by the present invention, the medical tape obtained by the present invention can be used as a patch by blending percutaneously absorbable drugs in the adhesive portion. Providing a pad to the medical tape of the present invention ensures a usage as a treatment product.

INDUSTRIAL APPLICABILITY

The medical tape manufactured using the film-forming base portion, obtained by the present invention has an extremely high effect of alleviating the persistent skin irritation during the application duration caused by the residual shrink force associated with the forming shrinkage of the support-bonded medical tape using inelastic material as the support in the prior art, in particular, the medical tape that has the forming shrinkage by using the solution polymer as the raw material and simultaneously performing the film formation and the lamination in the manufacturing process so as to be applicable on the skin that exhibits an excessive reaction even with an insignificant irritation. In addition, preventions of a skin trouble, a medical instrument pressure-related wound, and the like caused by the persistent skin irritation during the application duration can be expected. Furthermore, it is possible to provide a low-irritation medical tape, patch or the like. Therefore, the medical tape according to the present invention will greatly contribute to the medical industries.

REFERENCE SIGNS LIST 1 film-forming base portion
2 elastic base member portion
3 adhesion portion
4 release portion
5 support portion
6 solution polymer

The invention claimed is:

1. A method for manufacturing a medical tape, comprising:

applying a solution polymer serving as an elastic base member portion having an elastic function to an upper layer of a film-forming base portion having an inelastic function to form a film of the solution polymer;

laminating an adhesion portion having a function to apply and hold the elastic base member portion to a skin on an upper layer of the elastic base member portion, and laminating a release portion having a function to protect the adhesion portion on an upper layer of the adhesion portion;

peeling and removing the film-forming base portion from the elastic base member portion to obtain the elastic base member portion in a state where a residual shrink force generated by a forming shrinkage of the solution polymer is reduced and to obtain a three-layer structure consisting of the elastic base member portion, the adhesion portion, and the release portion; and laminating a support portion having a function to hold the elastic base member portion on the elastic base member portion of the three-layer structure.

* * * * *